US007101559B2

(12) United States Patent
McFadden et al.

(10) Patent No.: US 7,101,559 B2
(45) Date of Patent: Sep. 5, 2006

(54) IMMUNOMODULATORY PROTEIN AND USEFUL EMBODIMENTS THEREOF

(75) Inventors: Grant McFadden, London (CA); Alexandra Lucas, London (CA); Xing Li, London (CA)

(73) Assignee: Viron Therapeutics, Inc., London (CA)

( * ) Notice: Subject to any disclaimer, the term of this patent is extended or adjusted under 35 U.S.C. 154(b) by 211 days.

(21) Appl. No.: 10/455,000

(22) Filed: Jun. 4, 2003

(65) Prior Publication Data

US 2004/0038203 A1 Feb. 26, 2004

Related U.S. Application Data

(63) Continuation-in-part of application No. PCT/CA01/01734, filed on Dec. 4, 2001.

(60) Provisional application No. 60/251,147, filed on Dec. 4, 2000.

(51) Int. Cl.
*A61K 39/12* (2006.01)
(52) U.S. Cl. ................. 424/204.1; 424/229; 424/232.1
(58) Field of Classification Search ............. 424/204.1, 424/229.1, 232.1; 435/6, 69.1
See application file for complete search history.

(56) References Cited

U.S. PATENT DOCUMENTS

| | | | |
|---|---|---|---|
| 5,651,972 A * | 7/1997 | Moyer et al. ............. 424/199.1 |
| 5,656,465 A | 8/1997 | Panicali et al. | |
| 5,686,409 A | 11/1997 | McFadden et al. | |
| 5,834,419 A | 11/1998 | McFadden et al. | |
| 5,871,740 A | 2/1999 | Smith | |
| 5,939,525 A | 8/1999 | McFadden et al. | |
| 6,495,515 B1 | 12/2002 | McFadden et al. | |
| 6,562,376 B1 | 5/2003 | Hooper et al. | |
| 6,589,933 B1 | 7/2003 | McFadden et al. | |
| 6,894,155 B1 | 5/2005 | McFadden et al. | |
| 2004/0038203 A1 | 2/2004 | McFadden et al. | |

FOREIGN PATENT DOCUMENTS

| | | |
|---|---|---|
| WO | WO 91/16431 | 10/1991 |
| WO | WO 92/17583 | 10/1992 |
| WO | WO 96/33730 | 10/1996 |
| WO | WO 97/11714 | 4/1997 |
| WO | WO 97/44054 | 11/1997 |

OTHER PUBLICATIONS

Amano et al. Journal of General Virology, 1995, vol. 76, 1109-1115.*
Ahuja et al., "Chemokine Receptors and Molecular Mimicry," *Immunol. Today* 15:281-287 (1994).
Alcami and Smith, "Soluble Interferon-Gamma Receptors Encoded by Poxviruses," *Comp Immunol. Microbiol. Infect. Dis.* 19:305-317 (1996).
Alcami and Smith, "Vaccinia, Cowpox, and Camelpox Viruses Encode Soluble Gamma Interferon Receptors with Novel Broad Species Specificity," *J. Virol.* 69:4633-4639 (1995).
Alcami and Smith, "Receptors for Gamma-Interferon Encoded by Poxviruses: Implications for the Unknown Origin of Vaccinia Virus," *Trends Microbiol.* 4:321-326 (1996).
Amano et al., "Indentification and Characterization of the Thymidine Kinase Gene of Yaba Virus," *J. Gen. Virol.* 76:1109-1115 (1995).
Barinaga, "Viruses Launch Their Own 'Star Wars'," *Science* 258:1730-1731 (1992).
Born et al., "A Poxvirus Protein that Binds to and Inactivates IL-18, and Inhibits NK Cell Response.," *J. Immunol.* 164:3246-54 (2000).
Brunetti et al., "A Secreted High-Affinity Inhibitor of Human TNF from Tanapox Virus," *Proc. Natl. Acad. Sci. U.S.A.* 100:4831-4836 (2003).
Calderara et al., "Orthopoxvirus IL-18 Binding Proteins: Affinities and Antagonist Activities," *Virol.* 279: 22-26 (2001).
Chaudhuri et al., "Expression of the Duffy Antigen in K562 Cells. Evidence that it is the Human Erythrocyte Chemokine Receptor," *J. Biol. Chem.* 269:7835-7838 (1994).
Elsner et al., "Eotaxin-2 Activates Chemotaxis-Related Events and Release of Reactive Oxygen Species via Pertussis Toxin-Sensitive G Proteins in Human Eosinophils," *Eur. J. Immunol.* 28:2152-2158 (1998).
Endres et al., "CD4-Independent Infection by HIV-2 is Mediated by Fusin/CXCR4," *Cell* 87: 745-756 (1996).
Essani et al., "Multiple Anti-Cytokine Activities Secreted from Tanapox Virus-Infected Cells," *Microb. Pathog.* 17:347-353 (1994).
Fenger and Rouhandeh, "Proteins of Yaba Monkey Tumor Virus I. Structural Proteins," *J. Virol.* 18:757-764 (1976).
Gene Bank Sequence, AB015885.
Gene Bank Sequence, AF153912.
Gene Bank Sequence, AJ293568.
Gene Bank Sequence, D26580.
Graham et al., "Myxoma Virus M11L ORF Encodes a Protein for Which Cell Surface Localization is Critical in Manifestation of Viral Virulence," *Virol.* 191:112-124 (1992).
Graham et al., "The T1/35kDa Family of Poxvirus-Secreted Proteins Bind Chemokines and Modulate Leukocyte Influx into Virus-Infected Tissues," *Virol.* 229:12-24 (1997).
Hoffman and Karpus, "Chemokine Regulation of CNS T-Cell Infiltration in Experimental Autoimmune Encephalomyelitis," *Res. Immunol.* 149:790-794(1998).
Horuk, "Molecular Properties of the Chemokine Receptor Family," *Trends Pharmacol. Sci.* 15:159-165 (1994).
Hu et al., "Cowpox Virus Contains Two Copies of an Early Gene Encoding a Soluble Secreted Form of the Type II TNF Receptor," *Virol.* 204:343-356 (1994).
Jackson et al., "Expression of Mouse Interleukin-4 by a Recombinant Ectromelia Virus Suppresses Cytolytic Lymphocyte Responses and Overcomes Genetic Resistance to Mousepox," *J. Virol.* 75:1205-1210 (2001).
Knight et al., "Studies on Tanapox Virus," *Virol.* 172:116-124 (1989).

(Continued)

Primary Examiner—Ali R. Salimi
(74) *Attorney, Agent, or Firm*—Clark & Elbing LLP; Kristina Bieker-Brady (57) ABSTRACT

The invention generally features the use of Yaba monkey tumor virus nucleic acid molecules and polypeptides for the treatment or prevention of immune-related diseases.

19 Claims, 2 Drawing Sheets

OTHER PUBLICATIONS

Figure 1:
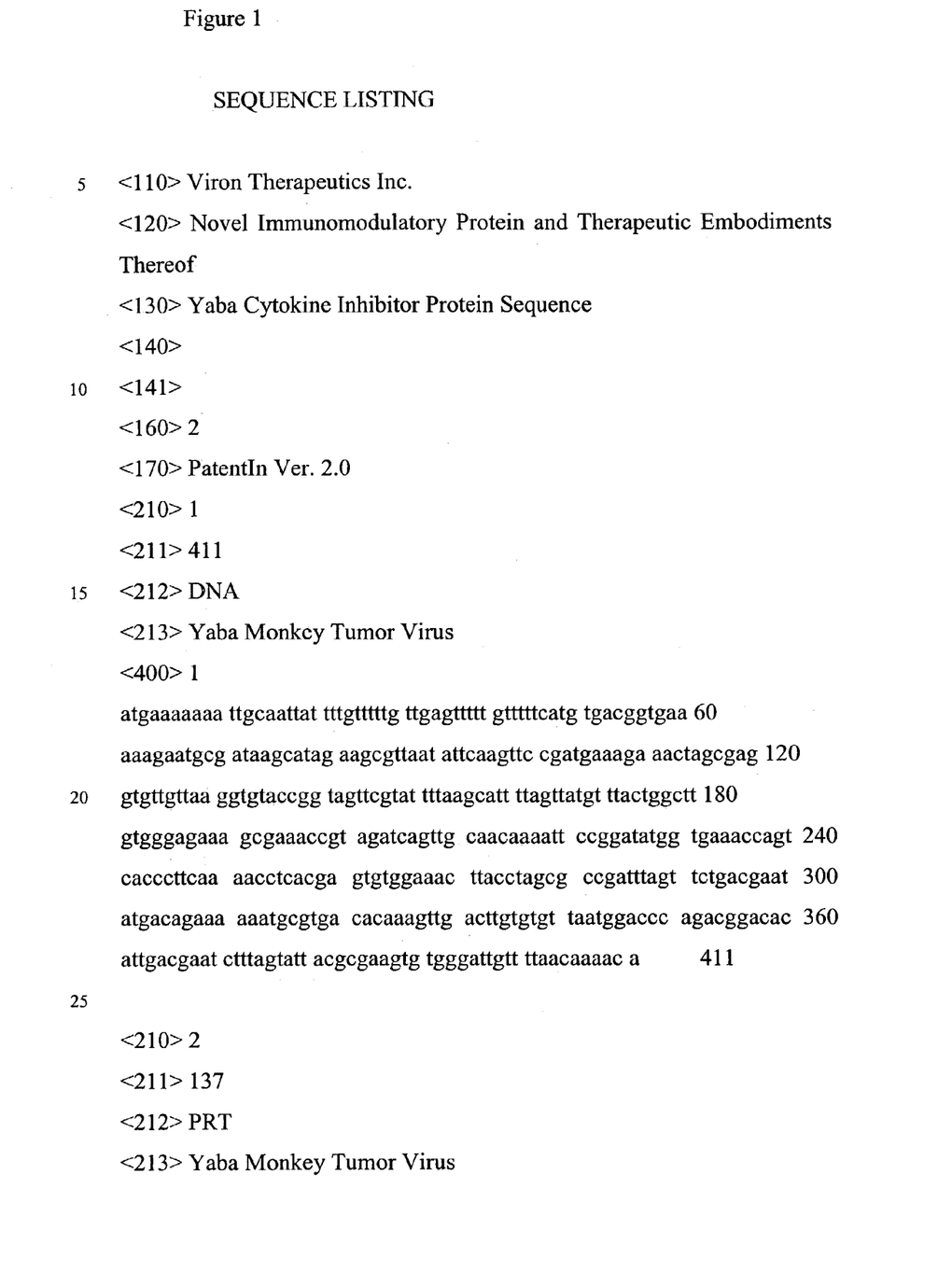

Kotwal and Jayaraman, "Regulation of Cytokine Secretion by Poxvirus Encoded Proteins," *Adv. In. Exp. Med. Biol.* 351:187(1992).

Lee et al., "The Genome Sequence of Yaba-Like Disease Virus, a Yatapoxvirus," *Virol.* 281:170-192 (2001).

Lee and Smith, "The Sequence of Yaba-Like Disease Virus, A Yatapoxvirus," XIIIth International Poxvirus-Iridovirus Symposium, Sep. 2-6, 2000.

Lee et al., "Studies of Yaba-Like Disease Virus, a Yatapoxvirus," *University of Oxford, Thesis* pp. 15-27 and 191-239 (Sep. 25, 2000).

Lomas et al., "Inhibition of Plasmin, Urokinase, Tissue Plasminogen Activator, and $C_{15}$ by a Myxoma Virus Serine Proteinase Inhibitor," *J. Biol. Chem.* 268:516-521 (1993).

Macen et al., "SERP1, a Serine Proteinase Inhibitors Encoded by Myxoma Virus, is a Secreted Glycoprotein that Interferes with Inflammation," *Virol.* 195:348-363 (1993).

McFadden, "Rabbit, Hare, Squirrel and Swine Poxviruses," *Encyclopedia of Virology* pp. 1153-1160 (1997).

McFadden et al., "Myxoma T2 Proteins as a Model for Poxvirus TNF Receptor Homologs, " *J. Neuroimmunol.* 72:119-126 (1997).

McFadden et al., "Interruption of Cytokine Networks by Poxviruses: Lessons from Myxoma Virus," *J. Leukocyte Biol.* 57:731-738 (1995).

Moss et al., "Immune-Defense Molecules of Molluscum Contagiosum Virus, a Human Poxvirus," *Trends Microbiol.* 8:473-477 (2000).

Mossman et al., "Myxoma Virus M-T7, a Secreted Homolog of the Interferon-Gamma Receptor, is a Critical Virulence Factor for the Development of Myxomatosis in European Rabbits," *Virol.* 215:17-30 (1996).

Mossman et al., "Species Specificity of Ectromelia Virus and Vaccinia Virus Interferon-Gamma Binding Proteins," *Virol.* 208:762-769 (1995).

Mossman et al., "Interferon-Gamma Receptors Encoded by Poxviruses," *Viroreceptors, Virokines And Related Immune Modulators Encoded by DNA Viruses*, Ed: McFadden, R.G. Landers Co. Chapter 4, pp. 41-54 (1994).

Neote et al., "Molecular Cloning, Functional Expression, and Signaling Characteristics of a C-C Chemokine Receptor," *Cell* 72:415-425 (1993).

Neurath et al., "Search for Hepatitis B Virus Cell Receptors Reveals Binding Sites for Interleukin 6 on the Virus Envelope Protein," *J. Exp. Med.* 175:461-469 (1992).

Olsen and Yohn, "Immunodiffusion Analysis of Yaba Poxvirus Structural and Associated Antigens," *J. Virol.* 5:212-220 (1970).

Opgenorth et al., "Deletion of the Growth Factor Gene Related to EGF and TGFα Reduces Virulence of Malignant Rabbit Fibroma Virus," *Virol.* 186:175-191 (1992).

Opgenorth et al., "Deletion Analysis of Two Tandemly Arranged Virulence Genes in Myxoma Virus, M11L and Myxoma Growth Factor," *J. Virol.* 66:4720-4731 (1992).

Opgenorth et al., "Transforming Growth Factor Alpha, Shope Fibroma Growth Factor, and Vaccinia Growth Factor can Replace Myxoma Growth Factor in the Induction of Myxomatosis in Rabbits," *Virol.* 192:701-709 (1993).

Paulose et al., "Selective Inhibition of a TNF-α Induced Cell Adhesion Molecule Gene Expression by Tanapox Virus," *Microb. Pathog.* 25:33-41 (1998).

Powell et al., "An I-Kappa-B Homolog Encoded by African Swine Fever Virus Provides a Novel Mechanism for Downregulation of Proinflammatory Cytokine Responses in Host Macrophages," *J. Virol.* 70:8527-8533 (1996).

Riffkin et al., "A Single Amino-Acid Change Between the Antigenically Different Extracellular Serine Proteases V2 and B2 from *Dichelobacter nodosus*," *Gene* 167:279-283 (1995).

Schreiber and McFadden, "The Myxoma Virus TNF-Receptor Homologue (T2) Inhibits Tumor Necrosis Factor-Alpha in a Species-Specific Fashion," *Virol.* 204:692-705 (1994).

Sedger and McFadden, "M-T2: A Poxvirus TNF Receptor Homologue with Dual Activities," *Immunol. Cell Biol.* 74:538-545 (1996).

Senkevich et al., "Genome Sequence of a Human Tumorigenic Poxvirus: Prediction of Specific Host Response-Evasion Genes," *Science* 273:813-816 (1996).

Senkevich et al., "The Genome of Molluscum Contagiosum Virus: Analysis and Comparison with Other Poxviruses," *Virol.* 233:19-42 (1997).

Smith et al., "Ectromelia, Vaccinia and Cowpox Viruses Encode Secreted Interleukin-18-Binding Proteins," *J. Gen. Virol.* 81:1223-1230 (2000).

Smith et al., "T2 Open Reading Frame From the Shope Fibroma Virus Encodes a Soluble Form of the TNF Receptor," *Biochem. Biophys. Res. Commun.* 176:335-342 (1991).

Smith, "Virus Proteins that Bind Cytokines, Chemokines, or Interferons," *Curr. Opin. Immunol.* 8:467-471 (1996).

Symones et al., "The Vaccinia Virus C12L Protein Inhibits Mouse IL-18 and Promotes Virus Virulence in the Murine Intranasal Model," *J. Gen. Virol.* 83:2833-44 (2002).

Symons et al., "Vaccinia Virus Encodes a Soluble Type I Interferon Receptor of Novel Structure and Broad Species Specificity," *Cell* 81:551-560 (1995).

Thompson, "Human Gene Therapy Harsh Lessons, High Hopes," *FDA Consum.* 34:19-24 (2000).

Trkola et al., "CD4-Dependent, Antibody-Sensitive Interactions Between HIV-1 and Its Co-Receptor CCR-5," *Nature* 384:184-187 (1996).

Upton et al., "Tumorigenic Poxviruses: Genomic Organization and DNA Sequence of the Telomeric Region of the Shope Fibroma Virus Genome," *Virol.* 160:20-30 (1987).

Upton et al., "Myxoma Virus Expresses a Secreted Protein with Homology to the Tumor Necrosis Factor Receptor Gene Family that Contributes to a Viral Virulence," *Virol.* 184:370-382 (1991).

Upton et al., "Encoding of a Homology of the IFN-Gamma Receptor by Myxoma Virus," *Science* 258:1369-1372 (1992).

Upton et al., "Mapping and Sequence of a Gene from Myxoma Virus That is Related to Those Encoding Epidermal Growth Factor and Transforming Growth Factor Alpha," *J. Virol.* 61:1271-1275 (1987).

Upton et al., "Myxoma Virus and Malignant Rabbit Fibroma Virus Encode a Serpin-Like Protein Important for Virus Virulence," *Virol.* 179:618-631 (1990).

Upton and McFadden, "Detection of Viral Homologs of Cellular Interferon Gamma Receptors," *Methods in Molecular Genetics* 4:383-390, Molecular Virology Techniques Part A, eds. Adolph, Academic Press Inc. (1994).

Vinyals et al., "Failure of Wild-Type p53 Gene Therapy in Human Cancer Cells Expressing a Mutant p53 Protein," *Gene Ther.* 6:22-33 (1999).

Xiang and Moss, "Correspondence of the Functional Epitopes of Poxvirus and Human Interleukin-18-Binding Proteins," *J. Virol.* 75:9947-9954 (2001).

Xiang and Moss, "Determination of the Functional Epitopes of Human Interleukin-18-Binding Protein by Site-Directed Mutagenesis," *J. Biol. Chem.* 276:17380-17386 (2001).

Xiang and Moss, "Identification of Human and Mouse Homologs of the MC51L-53L-54L Family of Secreted Glycoproteins Encoded by the Molluscum Contagiosum Poxvirus," *Virol.* 257:297-302 (1999).

Xiang and Moss, "IL-18 Binding and Inhibition of Interferon Gamma Induction by Human Poxvirus-Encoded Proteins," *Proc. Natl. Acad. Sci. U.S.A.* 96:11537-11542 (1999).

Xiang and Moss, "Molluscum Contagiosum Virus Interleukin-18 (IL-18) Binding Protein is Secreted as a Full-Length Form That Binds Cell Surface Glycosaminoglycans Through the C-Terminal Tail and a Furin-Cleaved Form with Only the IL-18 Binding Domain," *J. Virol.* 77:2623-30 (2003).

Wu et al., "CD4-Induced Interactions of Primary HIV-1 gp120 Glycoproteins with the Chemokine Receptor CCR-5," *Nature* 384:179-183 (1996).

International Search Report for WO 02/046214.

* cited by examiner

Figure 1

SEQUENCE LISTING

<110> Viron Therapeutics Inc.

<120> Novel Immunomodulatory Protein and Therapeutic Embodiments Thereof

<130> Yaba Cytokine Inhibitor Protein Sequence

<140>

<141>

<160> 2

<170> PatentIn Ver. 2.0

<210> 1

<211> 411

<212> DNA

<213> Yaba Monkey Tumor Virus

<400> 1
atgaaaaaaa ttgcaattat tttgtttttg ttgagttttt gtttttcatg tgacggtgaa 60
aaagaatgcg ataagcatag aagcgttaat attcaagttc cgatgaaaga aactagcgag 120
gtgttgttaa ggtgtaccgg tagttcgtat tttaagcatt ttagttatgt ttactggctt 180
gtgggagaaa gcgaaaccgt agatcagttg caacaaaatt ccggatatgg tgaaaccagt 240
caccccttcaa aacctcacga gtgtggaaac ttacctagcg ccgatttagt tctgacgaat 300
atgacagaaa aaatgcgtga cacaaagttg acttgtgtgt taatggaccc agacggacac 360
attgacgaat ctttagtatt acgcgaagtg tgggattgtt ttaacaaaac a     411

<210> 2

<211> 137

<212> PRT

<213> Yaba Monkey Tumor Virus

Figure 1 (Cont'd)

<400> 2

Met Lys Lys Ile Ala Ile Ile Leu Phe Leu Leu Ser Phe Cys Phe Ser
1               5               10              15

Cys Asp Gly Glu Lys Glu Cys Asp Lys His Arg Ser Val Asn Ile Gln
        20              25              30

Val Pro Met Lys Glu Thr Ser Glu Val Leu Leu Arg Cys Thr Gly Ser
        35              40              45

Ser Tyr Phe Lys His Phe Ser Tyr Val Tyr Trp Leu Val Gly Glu Ser
        50              55              60

Glu Thr Val Asp Gln Leu Gln Gln Asn Ser Gly Tyr Gly Glu Thr Ser
        65              70              75              80

His Pro Ser Lys Pro His Glu Cys Gly Asn Leu Pro Ser Ala Asp Leu
            85              90              95

Val Leu Thr Asn Met Thr Glu Lys Met Arg Asp Thr Lys Leu Thr Cys
            100             105             110

Val Leu Met Asp Pro Asp Gly His Ile Asp Glu Ser Leu Val Leu Arg
            115             120             125

Glu Val Trp Asp Cys Phe Asn Lys Thr
            130                         135

IMMUNOMODULATORY PROTEIN AND USEFUL EMBODIMENTS THEREOF

CROSS REFERENCE TO RELATED APPLICATIONS

This application is a continuation-in-part of International Application No. PCT/CA01/01734, filed Dec. 4, 2001, published in English under PCT article 21(2), currently pending, which claims benefit of U.S. provisional application 60/251,147, filed Dec. 4, 2000, each of which are hereby incorporated by reference.

FIELD OF THE INVENTION

This invention relates to a novel secreted viral protein that may be utilized in the treatment of human diseases. The protein disclosed herein is isolated from the genome of the poxvirus family, where said virus is the Yaba Monkey Tumor Virus. This invention reveals the non-obvious discovery of the sequence of this novel immunomodulatory protein and useful embodiments thereof that may mediate an anti-inflammatory and/or immunomodulatory role when administered in vivo.

BACKGROUND OF THE INVENTION

Poxviruses are a large family of DNA viruses known to infect a variety of mammalian species. To date, approximately 50 poxvirus genomes have been identified and each genome contains about 200 open reading frames encoded therein. The poxvirus family, otherwise known as Poxviridae, includes two subfamilies (Chordopoxvirinae and Entomopoxvirinae) wherein the species are divided into eight and three genuses respectively, including but limited to Orthopoxvirus, Parapoxvirus, Avipoxvirus, Capripoxvirus, Leporipoxvirus, Suipoxvirus, Molluscipoxvirus and Yatapoxvirus, which include but are not limited to the species known as Myxoma Virus, Vaccinia Virus, Swinepox Virus, Molluscum Contagiosum Virus and Yaba Monkey Tumor Virus. Poxviruses are characterized as large, brick-like virions with complex symmetry that share antigenic determinants among different species of the family.

It is well known within the art that, upon infection of a host organism, the poxvirus genome mediates expression of numerous proteins that interfere and modulate homeostasis within the host. In addition to proteins that mediate an intracellular effect, poxviruses are also known to secrete proteins into the circulatory system of the infected animal. Such secreted proteins include agents that bind and inhibit various different aspects of the mammalian immune system and minimize immune-mediated clearance of the virus.

The Yaba Monkey Tumor Virus (YMTV) is poxvirus of the Yatavirus genus and was characterized in 1958 during outbreaks of rhesus monkeys. YMTV infection in monkeys leads to epidermal histiocytomas that advance to suppurative inflammatory reactions. YMTV has a DNA genome of 136 kilobases with a large part of the genome yet to be cloned and characterized. YMTV grows relatively slowly in primate cell culture lines and its host range is restricted to a small number of primates, and occasionally man following accidental exposure to infected monkeys.

IL-18 is a pro-inflammatory mammalian cytokine that plays an important early function in the potentiation of $T_h1$-like immune responses. In addition to its independent effects, IL-18 synergizes with IL-12 to induce IFN-γ production from various immune cell types. Binding of IL-18 to specific cell-surface receptors induces NF-κB activation and IL-18 is important in vivo for production of IFN-γ and inflammatory responses that may contribute to inflammatory disease. These diseases include but are not limited to allergic inflammation, atherosclerotic plaque growth and unstable plaque rupture, arterial restenosis, by-pass graft occlusion, Gaucher's disease, diabetes mellitus, rheumatoid arthritis, multiple sclerosis, transplant rejection, transplant vasculopathy and glomerulonephritis.

This invention provides the non-obvious identification and characterization of a protein derived from YMTV, where said protein is referred to as YMTV Cytokine Inhibitor, or YCI. The invention embodies nucleic acid and amino acid polymers encoding said YCI, including methods of detecting and producing said YCI. The invention further embodies the use of this YCI as a method of modulating the immune response within an organism. It is further claimed herein that the nucleic acid and amino acid sequences disclosed may be utilized for the treatment of human individuals for the purpose of preventing, treating or reversing the onset of one or more immune-related diseases, including inflammation and the immune-mediated diseases outlined above, but not limited to such.

BRIEF DESCRIPTION OF THE DRAWINGS

The present invention will be further understood and supported using the following drawings and their associated descriptions. These descriptions and drawings are not meant to limit the invention by any circumstance and are to be interpreted as possible embodiments of the invention disclosed herein. The methods utilized in the generation of the data represented by these drawings are commonly known within the art and may be reproduced identically by employing the methods described herein.

FIG. 1 illustrates the genomic nucleic acid sequence of the YCI gene within YMTV, hereinafter referred to as "SEQ ID NO:1" and further illustrates the amino acid sequence of YCI protein expressed by YMTV, hereinafter referred to as "SEQ ID NO:2".

SUMMARY OF THE INVENTION

The invention disclosed herein characterizes a novel nucleic acid and protein sequence derived from the Yaba Monkey Tumor Virus (YMTV). The invention embodies all compositions associated with said sequences, including but not restricted to DNA and RNA fragments derived thereof, as well as amino acid sequences derived of the disclosed sequence. It is contemplated herein that the disclosed protein sequence, as well as homologs, analogs and fragments thereof, are capable of binding aspects of the mammalian immune system with detectable affinity and stability. In one such embodiment, such binding occurs between the disclosed protein and one or more mammalian cytokines, where one such cytokine is interleukin-18, or IL-18 as known within the art. The disclosed protein is therefore herein referred to as YMTV Cytokine Inhibitor, or YCI. The invention further embodies use of said YCI nucleic acid, including complimentary sequences thereto, and protein sequences for a variety of diagnostic and therapeutic applications. In one such embodiment, it is contemplated herein that YCI sequences may be utilized to identify interactions with immune related proteins. In a further embodiment, the YCI sequences disclosed herein may be introduced into a mammalian organism for the purpose of modulating the incidence, progression and pathogenesis of an inflammatory, auto-immune or immune-mediated disease condition within said organism.

In one aspect, the invention features a purified nucleic acid molecule derived from the Yaba Monkey Tumor Virus, as defined by the following, including a fragment, homolog and analog of SEQ ID NO:1. In one embodiment, the nucleic acid molecule contains a sequence complementary to the following, or a fragment, analog and homolog of SEQ ID NO:1. In another embodiment, the nucleic acid molecule contains a where each T is replaced with a U. In another embodiment, the nucleic acid molecule is a recombinant nucleic acid vector containing SEQ ID NO:1, or one or more nucleic acid sequences encoding this nucleic acid sequence.

In another aspect, the invention features a host cell (e.g., a eukaryotic cell, a prokaryotic cell, a mammalian cell, a human cell containing a nucleic acid sequence of any of the previous aspects, or a fragment, analog and homolog thereof.

In a related aspect, the invention features a protein molecule encoded by the nucleic acid sequences, or fragments, analogs and homologs thereof, of any of the previous aspects.

In another aspect, the invention features an antibody molecule, or fragment thereof, having specificity against an epitope of a protein molecule of any of the previous aspects (e.g., SEQ ID NO:2). In one embodiment, the protein is conjugated with a protein or non-protein based moiety. In another embodiment, antibody is labeled with protein and/or non-protein moieties.

In another aspect, the invention features a method of modulating chemokine function through expression of one or more nucleic acid sequences of any of the previous aspects. In one embodiment, chemokine function is modulated through an interaction between proteins of any of the previous aspects, where the proteins non-covalently bind one or more mammalian chemokine(s).

In a related aspect, the invention features a method of modulating cytokine function through expression of one or more nucleic acid sequences of any previous aspect.

In a related aspect, the invention features a method of modulating cytokine function through interaction between the proteins of any of the previous aspects, where the proteins non-covalently bind one or more mammalian cytokine(s).

In another related aspect, the invention features a method of modulating chemokine receptor function through expression of one or more nucleic acid sequences of any of the previous aspects.

In yet another related aspect, the invention features a method of modulating chemokine receptor function through an interaction between the proteins of any of the previous aspects, where the proteins non-covalently bind one or more mammalian chemokine receptor(s).

In another aspect, the invention features a method of identifying substances that may bind the protein molecules encoded by a nucleic acid molecule of any previous aspect.

In another aspect, the invention features a method of identifying agents that modulate the transcription of the nucleic acids of any previous aspect.

In another aspect, the invention features a method of identifying agents that modulate the translation of protein(s) of any previous aspect.

In another aspect, the invention features a A method of identifying agents that modulate post-translational modification of protein(s) of any previous aspect.

In another aspect, the invention features a composition for the treatment of inflammation in mammalian organisms comprising a nucleic acid molecule of any previous aspect.

In another aspect, the invention features a composition for the treatment of inflammation in mammalian organisms (e.g., humans, rats, mice, horses, cows, dogs, cats, goats, or sheep), where the composition contains the protein(s) of any previous aspect.

In another aspect, the invention features a composition for the treatment of human disorders mediated by inflammation, where the composition contains the nucleic acid molecule of any previous aspect.

A composition for the treatment of human disorders mediated by inflammation, where the composition contains the protein(s) of any previous aspect.

A composition for the treatment of human disorders mediated by autoimmunity, where the composition contains a nucleic acid molecule of any previous aspect.

In another aspect, the invention features a composition for the treatment of human disorders mediated by autoimmunity, where the composition contains the protein(s) of any previous aspect.

In another aspect, the invention features a composition for the prevention of human disorders associated with inflammation, where the composition contains a nucleic acid molecule of any previous aspect.

In another aspect, the invention features a composition for the prevention of human disorders associated with inflammation, where the composition contains the protein(s) of any previous aspect.

In another aspect, the invention features a composition for the prevention of human disorders associated with autoimmunity, where the composition contains a nucleic acid molecule of any previous aspect.

In another aspect, the invention features a composition for the prevention of human disorders associated with autoimmunity, where the composition contains a protein(s) of any previous aspect. In another aspect, the invention features a composition for the treatment of a human disorder, where the disorder is either allergic inflammation, asthma, psoriasis, diabetes mellitus, rheumatoid arthritis, multiple sclerosis, lupus erythmateous, transplant rejection, graft rejection, glomerulonephritis, arterial restenosis, coronary occlusion, transplant vasculopathy, atherosclerosis, unstable atherosclerotic plaque rupture, ischemic reperfusion injury, or glomerulonephritis. In one embodiment, the disorder is of a chronic nature. In another embodiment, the disorder is of an acute or sub-acute nature.

In another aspect, the invention features a method of treating a mammal having an immunomodulatory disorder, the method comprising administering to a mammal a therapeutically effective amount of a compound containing a nucleic acid molecule or polypeptide of any previous aspect, where the compound has an immunomodulatory effect in the mammal. In one embodiment, the disorder is selected from the group consisting of allergic inflammation, asthma, psoriasis, diabetes mellitus, rheumatoid arthritis, multiple sclerosis, lupus, erythmateous, transplant rejection, graft rejection, glomerulonephritis, arterial restenosis, coronary occlusion, transplant vasculopathy, atherosclerosis, unstable atherosclerotic plaque rupture, ischemic reperfusion injury, and glomerulonephritis.

In another aspect, the invention features a substantially pure Yatapoxvirus cytokine inhibitor polypeptide.

In another aspect, the invention features a substantially pure Yatapoxvirus nucleic acid molecule, where the nucleic acid molecule encodes a Yatapoxvirus cytokine inhibitor polypeptide. In one embodiment, the the nucleic acid molecule is selected from genomic DNA, cDNA, and mRNA.

In another aspect, the invention features a vector comprising the nucleic acid molecule a nucleic acid molecule of any previous aspect. In one embodiment, the vector is a gene therapy vector.

In another aspect, the invention features a cell comprising the vector of the previous aspect. In one embodiment, the nucleic acid molecule is operably linked to regulatory sequences for expression of Yatapoxvirus cytokine inhibitor polypeptide and the regulatory sequences contain a promoter.

In another aspect, the invention features a non-human transgenic animal comprising the nucleic acid of any of the previous aspects.

In another aspect, the invention features a cell from the non-human transgenic animal of the previous aspect.

In another aspect, the invention features a non-human transgenic animal having a knockout mutation in one or both alleles encoding a polypeptide substantially identical to a Yatapoxvirus cytokine inhibitor polypeptide.

In another aspect, the invention features a probe for analyzing a Yatapoxvirus gene or a Yatapoxvirus gene homolog or fragment thereof, the probe having at least 50% nucleotide sequence identity to a sequence encoding a Yatapoxvirus cytokine inhibitor polypeptide or fragment thereof, where the polypeptide fragment contains at least six amino acids, and the probe hybridizes under high stringency conditions to at least a portion of a Yatapoxvirus nucleic acid molecule.

In another aspect, the invention features a kit for the analysis of a Yatapoxvirus nucleic acid molecule, the kit comprising a nucleic acid molecule probe for analyzing a Yatapoxvirus nucleic acid molecule present in a test subject.

In another aspect, the invention features a kit for the analysis of a Yatapoxvirus cytokine inhibitor polypeptide, the kit comprising an antibody for analyzing a Yatapoxvirus cytokine inhibitor polypeptide present in a test subject.

In another aspect, the invention features a purified nucleic acid molecule derived from the Yaba Monkey Tumor Virus having homology to at least a fragment of SEQ ID NO:1. In one embodiment, the nucleic acid molecule has at least 85% nucleic acid sequence identity to SEQ ID NO:1. In another embodiment, the nucleic acid molecule has at least 95% nucleic acid sequence identity to SEQ ID NO:1. In yet another embodiment, the nucleic acid molecule hybridizes to at least a fragment of SEQ ID NO:1. In yet another embodiment the nucleic acid molecule consists of SEQ ID NO:1. In another embodiment, the nucleic acid molecule contains a sequence complementary to at least a fragment of SEQ ID NO:1. In another embodiment, the nucleic acid molecule has each T replaced with a U.

In another aspect, the invention features a vector comprising the nucleic acid molecule of any of the previous aspect. In one embodiment, the nucleic acid molecule is positioned for expression. In another embodiment, the nucleic acid molecule is under the control of a promoter. In another embodiment, the vector is suitable for expression in a mammalian cell.

In another aspect, the invention features a host cell comprising the nucleic acid molecule of any of the previous aspects. In one embodiment, the cell is a mammalian cell. In another embodiment, the cell is a human cell. In yet another embodiment, the cell is in vivo.

In another aspect, the invention features a isolated protein molecule encoded by a nucleic acid sequence of any previous aspect. In one embodiment, the protein molecule contains the amino acid sequence of SEQ ID NO:2. In another embodiment, the protein molecule consists of the amino acid sequence of SEQ ID NO:2.

In another aspect, the invention features a pharmaceutical composition comprising the nucleic acid molecule of any previous aspect formulated in a pharmaceutically acceptable carrier in an amount sufficient to treat an immune disorder or inflammation when administered to a cell of a subject.

In another aspect, the invention features a pharmaceutical composition comprising the polypeptide of any previous aspect formulated in a pharmaceutically acceptable carrier in an amount sufficient to treat an immune disorder or inflammation when administered to a subject.

By "homolog" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 70%, more preferably 80% or 85%, and most preferably 90%, 95%, 98%, or 99% identical at the amino acid level or nucleic acid to a reference sequence.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "hybridize" is meant pair to form a double-stranded molecule between complementary polynucleotide, or portions thereof, under various conditions of stringency. (See, e.g., Wahl, G. M. and S. L. Berger (1987) *Methods Enzymol.* 152:399; Kimmel, A. R. (1987) *Methods Enzymol.* 152:507) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196: 180, 1977); Grunstein and Hogness (*Proc. Natl. Acad. Sci.*, USA 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

The following standard abbreviations are utilized throughout specification of the present invention and its included drawings: DNA—deoxyribonucleic acid; RNA—ribonucleic acid; C—cytosine; G—guanine; A—adenosine; T—thymidine; N—unknown; A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and pY, pTyr—phosphotyrosine.

DETAILED DESCRIPTION OF THE INVENTION

The invention disclosed hereinunder identifies a novel protein derived from the Yaba Monkey Tumor Virus, which is well known within the art as a member of the poxvirus family and a further subset of the Yatapoxvirus genus therein. Said Yaba Monkey Tumor Virus is hereinafter referred to as "YMTV". In particular, this invention discloses an immunomodulatory nucleic acid and amino acid sequence relating thereto, referred to as the Yaba Cytokine Inhibitor, where the nucleic acid sequence and amino acid sequences, including homologs, analogs and truncations thereof, are hereinafter collectively abbreviated as "YCI". The disclosure herein contains relevant nucleic acid and protein sequences of YCI within SEQ ID NO:1 and SEQ ID NO:2, respectively, as attached hereinafter. Thus, the YCI gene has a length of 411 nucleotides, corresponding to an amino acid sequence of 137 amino acids encoded therein.

The scope of this invention includes variations of the nucleic acid sequences defined as follows:
(1) truncations, analogs and homologs of the nucleic acid sequences provided in SEQ ID NO:1;
(2) nucleic acid sequences differing from SEQ ID NO:1 by substitution of a T with a U;
(3) nucleic acid sequences complimentary to either the full length of SEQ ID NO:1, or complimentary to nucleic acid fragments derived thereof;
(4) nucleic acid sequences that hybridize with the nucleic acid sequences represented within SEQ ID NO:1;
(5) nucleic acid sequences differing from the full length of SEQ ID NO:1 due to the degeneracy of the genetic code.

The term "nucleic acid" is intended to include DNA and RNA that can either be of single or double stranded structure. The term "protein" or "polypeptide" refers to amino acid polymers existing in an unfolded or folded spatial organization and with or without catalytic function. The term "antibody" refers to protein molecules derived from a polyclonal or monoclonal population of B cells of mammalian origin. The term "antibody fragment" refers to the aforementioned antibody molecules that have been cleaved into different segments and/or may be labeled with fluorochrome compounds for the purpose of detection. The term "chemokine" refers to all known chemotactic cytokines expressed within mammalian organisms that mediate the recruitment and infiltration of leukocytes into tissues. The term "chemokine" includes but is not limited to all mammalian members of the C, CC, CXC, and CXXXC families of chemotactic cytokines, classified within the art based upon the distribution of cystine residues therein. The term "chemokine receptor" refers to all known transmembrane proteins known within the art to interact with one or more chemokines. The term "chemokine receptor" shall include but is not limited to all chemokine receptors classified within the art as CR, CCR, CXCR and CXXXCR. The term "cytokine" refers to all human cytokines known within the art that bind extracellular receptors upon the cell surface and thereby modulate cell function, including but not limited to IL-1, IL-4, IL-6, IL-18, TNF-α and IFN-γ. The term "cytokine receptor" refers to all human cytokine receptors within the art that bind one or more cytokine(s), as defined hereinunder, including but not limited to receptors of IL-1, IL-4, IL-6, IL-18, TNF-α and IFN-γ.

In one embodiment, this invention contemplates a purified or isolated double stranded nucleic acid molecule formed through hydrogen bonding of the nucleic acid molecules specified in SEQ ID NO:1, or related truncations, homologs and analogs thereof, to a complimentary nucleic acid sequence.

The nucleic acid molecules specified herein as SEQ ID NO:1 may also be inserted into an expression vector that contains necessary elements upstream and downstream of the inserted nucleic acid for the transcription and translation of the inserted sequence within prokaryotic and eukaryotic cells. The invention embodies expression vectors which comprise a nucleic acid molecule specified in SEQ ID NO:1, or related truncations, homologs and analogs thereof, with one or more transcription and translation elements operatively linked to the nucleic acid molecule. Possible expression vectors include, but are not limited to, cosmids, plasmids and modified viral vectors (replication-defective retroviruses, adenoviruses and adeno-associated viruses).

Recombinant expression vectors may be used to prepare transformed cell lines expressing the proteins encoded within nucleic acid sequences specified herein by SEQ ID NO:1, or related truncations, homologs and analogs thereof. This invention provides cell lines, including eukaryotic and prokaryotic cell types, containing a recombinant nucleic acid molecule specified herein within SEQ ID NO:1, or related truncations, homologs and analogs thereof.

This invention also contemplates transgenic non-human animals whose germ cells and somatic cells contain a recombinant molecule comprising a nucleic acid molecule specified in SEQ ID NO:1, or a related truncation, analog or homolog thereof. Such sequences may be expressed in non-human species including but not limited to zebrafish, *xenopus, drosophila*, mice, rats, rabbits, sheep, pigs and chickens.

This invention also embodies YCI encoded by SEQ ID NO:2, or related homologs, truncations and analogs thereof. This invention embodies all post-translational modifications of YCI and related homologs, truncations and analogs thereof. Such post-translational modifications include, but are not limited to, glycosylation, myristylation, tyrosine phosphorylation, serine phosphorylation, threonine phosphorylation, ubiquitination and proteolytic degradation.

This invention also embodies a method of preparing YCI encoded by SEQ ID NO:2, or related truncations, analogs and homologs thereof. A method of preparing such protein molecules is embodied by (1) transferring a recombinant expression vector of the herein specified YCI encoded by SEQ ID NO:1, (2) selecting transformed host cells from untransformed cells, (3) culturing the host cell under conditions that allow or induce the expression of the specified YCI encoded by SEQ ID NO:1 and (4) isolation of YCI from cultured host cells using a suitable purification procedure. In such embodiments, YCI may be produced within either prokaryotic or eukaryotic host cells, as appropriate.

This invention also embodies the purification of YCI encoded by SEQ ID NO:2, or related truncations, analogs and homologs thereof. In one embodiment, physical and chemical characteristics of YCI as specified herein are utilized to separate said protein from other protein or non-protein molecules. Such physical and chemical characteristics include but are not limited to, density, molecular weight, isoelectric point, ligand affinity, solubility, temperature-sensitivity, etc.

This invention also contemplates the conjugation of YCI encoded by SEQ ID NO:2, or related truncations, analogs and homologs thereof, to other protein or non-protein molecules. This may be accomplished by covalent attachment of conjugating molecules to any residue of the specified YCI encoded by SEQ ID NO:2, or related truncations, analogs and homologs thereof.

This invention also contemplates antibodies or antibody-derived fragments specifically capable of binding the specified YCI encoded by SEQ ID NO:2 or any segment thereof. Therefore, this invention also provides a method of generating antibodies within mammalian species through injection of the specified YCI encoded by SEQ ID NO:2 or segments of the amino acid sequence thereof into a mammalian organism.

Furthermore, antibodies or antibody fragments specific for the specified YCI encoded by SEQ ID NO:2 or segments thereof may be labeled with detectable substances, such as fluorochromes or peroxidases, that permit detection of the YCI, or related sequences specified within SEQ ID NO:2, within tissues and cells. The invention also covers use of such antibodies to purify YCI or its related homologs, analogs and truncations from cells and tissues.

This invention also provides a method for the design and construction of nucleotide probes unique to nucleic acid molecules encoding YCI encoded by SEQ ID NO:1 or variations thereof. Such nucleotide probes may also be labeled with detectable substances that permit detection of YCI encoding nucleic acid sequences within tissues and cells. In addition, nucleotide probes may also be utilized as a diagnostic tool to assess the upregulation of YCI expression within cells. Labeled nucleotide probes may alternatively be used to identify YCI related nucleic acid molecules from a heterogeneous population of deoxyribonucleic acids and/or ribonucleic acids (e.g., a cDNA library, a genomic DNA library or a genomic RNA library).

This invention also embodies the use of the polymerase chain reaction or related polymerase reactions to amplify or generate nucleic acids encoding YCI, including related truncations, analogs or truncations thereof. In one embodiment, synthetic oligonucleotide primers generated from segments of the nucleotide sequence disclosed in SEQ ID NO:1 can be utilized to amplify YCI-encoding sequence(s) from genomic DNA, cDNA libraries, RNA molecules or other nucleic acid mixtures.

This invention also provides a method of modulating YCI expression within cells, tissues, organs and organisms. The introduction of nucleic acid molecules into cells and tissues may be utilized to amplify the transcription and translation of YCI-encoding nucleic acids or related truncations, analogs or homologs or related nucleic acid sequences as specified by SEQ ID NO:1. Alternatively, YCI expression may be downregulated by the introduction of complimentary nucleic acid sequences that block transcription and translation of YCI-encoding nucleic acids or related truncations, analogs or homologs or related nucleic acid sequences as specified by SEQ ID NO:1.

In a preferred embodiment, YCI encoded herein as SEQ ID NO:2 may bind one or more types of chemokines derived from or present within mammalian organisms. Therefore, YCI may be administered in vivo to bind one or more chemokine proteins within mammalian organisms. Furthermore, YCI may be administered or expressed within specific mammalian tissues to bind chemokines present within said tissue. It is envisioned herein that the binding between YCI and said chemokine shall reduce, inhibit and/or otherwise diminish the ability of said chemokine to conduct its normal function within mammalian organisms. In one embodiment, the binding between YCI and one or more chemokine(s) shall occur in the region of the chemokine molecule responsible for interaction with a corresponding receptor thereof, hence preventing the covalent or non-covalent interaction between said chemokine and its corresponding chemokine receptor.

In another preferred embodiment, YCI encoded herein as SEQ ID NO:2 may bind mammalian cytokines, other than those defined herein as chemokines. As such, YCI may be administered in vivo to bind one or more types of cytokines within mammalian organisms. Alternatively, YCI may be administered or expressed within specific mammalian tissues to bind cytokines, other than those herein defined as chemokines, within said tissue. It is envisioned herein that the binding between YCI and said cytokine shall reduce, inhibit and/or other diminish the ability of said cytokine to conduct its normal function within mammalian organisms. In one embodiment, the binding between YCI and one or more cytokine(s) shall occur in the region of the cytokine molecule responsible for interaction with a corresponding receptor thereof, hence preventing the covalent or non-covalent interaction between said cytokine and its corresponding cytokine receptor.

In another preferred embodiment, YCI encoded herein as SEQ ID NO:2 may bind mammalian chemokine receptors, as defined above. Such binding between YCI and one or more chemokine receptors may occur at the extracellular domain of said receptor. Furthermore, it is envisioned herein that such binding between YCI and one or more of the said chemokine receptors may disrupt normal signaling known within the art to occur upon engagement of said receptor with the appropriate chemokine ligand. As such, YCI encoded herein as SEQ ID NO:2 may be administered in vivo to bind one or more chemokine receptors and reduce, inhibit and/or other diminish the signaling functions mediated by such chemokine receptors.

This invention further provides a method for the identification of substances capable of binding YCI encoded herein as SEQ ID NO:2, or related truncations, analogs or homologs derived from viral, bacterial or mammalian sources. In one embodiment, YCI is present in proximity to other proteins derived from mammalian sources, including the appropriate conditions necessary for binding to occur, while binding is detected using YCI-specific labeled antibodies. In another embodiment, a yeast two hybrid assay system is utilized as a method for the identification of proteins interacting with YCI, its truncations, analogs or homologs derived from mammalian sources. In another embodiment, interactions between YCI and other proteins, including but not restricted to immune-related proteins, are detected through cross-linking agents as are known within the art that mediate covalent bonds between YCI and other proteins that demonstrate significant affinity thereto.

This invention further provides a method of identifying agents that affect the transcription and or translation of YCI encoding nucleic acids, including but not limited to those represented as SEQ ID NO:1 within cells expressing said protein, including truncations, analogs and homologs. In one embodiment, the pattern and level of YCI encoding RNA and full-length protein is assayed upon treatment of YCI expressing cells under assay conditions including, but not limited to, the treatment of YCI expressing cells with growth factors, hormones, cytokines, phorbol esters, hemagglutinins, antibodies and antibody fragments.

The invention herein also provides a method of identifying agents that modulate post-translational modification of YCI, including truncations, analogs and homologs. Such modifications may play a role in YCI protein functions, cytokine protein functions, chemokine protein functions, chemokine receptor functions and other functions or dysfunctions derived thereof. Examples of such modifications include, but are not limited to, protein folding, disulfide linkage, glycosylation, myristylation, palmitoylation, tyrosine phosphorylation, serine phosphorylation, threonine phosphorylation, ubiquitination and proteolytic degradation.

This invention also provides methods for the generation of experimental models for the study of YCI-encoding nucleic acid and protein functions in vivo or in vitro conditions. Cells, tissues and non-human animals that express, over-express or underexpress YCI-encoding nucleic acids, YCI or any related truncations, analogs or homologs thereof, can be established according to the embodiments of the invention herein. In particular, the generation of transgenic non-human animals may be accomplished via nuclear oocyte microinjection of YCI-encoding nucleic acids will provide novel models for the determination of YCI structure and function. This invention also permits the use of YCI-encoding nucleic acids to develop cell lines to study the effect of YCI expression, over-expression or under-expression in various developmental systems, including, but not limited to, hematopoesis, neurogenesis, mammary development and lung epithelial development, cell homeostasis, cell signaling, cell death, differentiation and neuronal development.

In addition, this invention contemplates human therapeutic uses derived from the herein disclosed YCI-encoding nucleic acids. In a preferred embodiment, the aforementioned methods are utilized to reduce, treat, prevent or otherwise lower human conditions associated or mediated by inflammation. In one preferred embodiment, the herein disclosed YCI-encoding nucleic acids are introduced into a mammalian animal through methods and procedures well known within the art. In such situations, it is envisioned that such nucleic acids shall be introduced into cells and tissues that shall mediate replication, transcription and/or translation of said nucleic acids. In another preferred embodiment, YCI-encoding nucleic acids are into specific tissue or cell type of a mammalian animal for the treatment, prevention and/or reduction of disease conditions associated with inflammation. In yet another preferred embodiment, YCI-encoding nucleic acids are introduced into cells and tissues while in vitro or ex vivo conditions, that shall mediate replication, transcription and/or transplantation of said nucleic acids, prior to the transplantation of such YCI-expressing cells and tissues into a mammalian organism for the purpose of reducing, treating, preventing and otherwise lowering disease conditions associated or mediated by inflammation.

The invention disclosed herein further contemplates human therapeutic uses derived from the herein disclosed YCI and/or modifications of the same through other embodiments described herein. In a preferred embodiment, the YCI disclosed herein, and related truncations, analogs and homologs thereof, are introduced into a mammalian organism for the purpose of treating, preventing, reducing or otherwise lowering disease conditions associated or mediated by inflammation. In one preferred embodiment, YCI disclosed herein, and related truncations, analogs and homologs thereof, are specifically introduced in vivo within a specific tissue type that is known within the art to be the site or location of a disease conditions associated or mediated by inflammation. In another embodiment, the YCI disclosed herein, and related truncations, analogs and homologs thereof, are introduced into cells and/or a tissue while in vitro or ex vivo conditions, prior to the transplantation of said cells and/or a tissue into a mammalian organism for the purpose of treating, preventing, reducing or otherwise lowering disease conditions associated or mediated by inflammation.

Further envisioned within the scope of this invention is the usage of the invention, its associated nucleic acids, proteins, antibodies, conjugates, analogs, homologs and truncations thereof, and of its embodiment for the treatment of all human diseases and/or conditions that are mediated or associated with the onset of inflammation, as well as human diseases and/or conditions that are mediated or associated with autoimmunity. Such diseases and/or conditions include but are not restricted to inflammation, autoimmune disease and immune-mediated disorders, which include but are not restricted to, allergic inflammation, arterial restenosis, by-pass graft occlusion, Gaucher's disease, diabetes mellitus, rheumatoid arthritis, multiple sclerosis, transplant rejection, transplant vasculopathy and glomerulonephritis.

This invention also contemplates that reagents suitable for the therapies and diagnostics outlined herein may be administered using pharmaceutically acceptable vehicles. Such vehicles include, but are not limited to, expression vectors, microinjection, liposome delivery, subcutaneous injection, intravenous injection, oral administration, inhalation, transdermal application or rectal administration. Such vehicles and related therapeutic regima maybe optimized for according to factors such as disease stage, age, sex and weight of the individual. In one embodiment, reagents suitable for the therapies and diagnostics outlined herein may be packaged into convenient kits providing the necessary materials packaged into suitable containers. Such kits may include suitable supports useful and assisting in performing the therapeutic and diagnostic strategies outlined herein.

Other objects, features and advantages of the present invention that become clear as a result of the methods provided herein and depicted in the enclosed drawings are included in this invention. It should be understood that examples and preferred embodiments of the invention herein are given by way of illustration and various alterations and modifications within the spirit of the invention are included as part of the invention herein. Those skilled in the art will recognize alterations and modifications of the invention herein that must however be respected as a part of the present invention.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

SEQUENCE LISTING

```
<160> NUMBER OF SEQ ID NOS: 2

<210> SEQ ID NO 1
<211> LENGTH: 411
<212> TYPE: DNA
<213> ORGANISM: Yaba Monkey Tumor Virus
<400> SEQUENCE: 1
atgaaaaaaa ttgcaattat tttgtttttg ttgagttttt gtttttcatg tgacggtgaa 60
aaagaatgcg ataagcatag aagcgttaat attcaagttc cgatgaaaga aactagcgag 120
gtgttgttaa ggtgtaccgg tagttcgtat tttaagcatt ttagttatgt ttactggctt 180
gtgggagaaa gcgaaaccgt agatcagttg caacaaaatt ccggatatgg tgaaaccagt 240
caccccttcaa aacctcacga gtgtggaaac ttacctagcg ccgatttagt tctgacgaat 300
atgacagaaa aaatgcgtga cacaaagttg acttgtgtgt taatggaccc agacggacac 360
attgacgaat ctttagtatt acgcgaagtg tgggattgtt ttaacaaaac a 411

<210> SEQ ID NO 2
<211> LENGTH: 137
<212> TYPE: PRT
<213> ORGANISM: Yaba Monkey Tumor Virus

<400> SEQUENCE: 2

Met Lys Lys Ile Ala Ile Ile Leu Phe Leu Leu Ser Phe Cys Phe Ser
1 5 10 15

Cys Asp Gly Glu Lys Glu Cys Asp Lys His Arg Ser Val Asn Ile Gln
20 25 30

Val Pro Met Lys Glu Thr Ser Glu Val Leu Leu Arg Cys Thr Gly Ser
35 40 45

Ser Tyr Phe Lys His Phe Ser Tyr Val Tyr Trp Leu Val Gly Glu Ser
50 55 60

Glu Thr Val Asp Gln Leu Gln Gln Asn Ser Gly Tyr Gly Glu Thr Ser
65 70 75 80

His Pro Ser Lys Pro His Glu Cys Gly Asn Leu Pro Ser Ala Asp Leu
85 90 95

Val Leu Thr Asn Met Thr Glu Lys Met Arg Asp Thr Lys Leu Thr Cys
100 105 110

Val Leu Met Asp Pro Asp Gly His Ile Asp Glu Ser Leu Val Leu Arg
115 120 125

Glu Val Trp Asp Cys Phe Asn Lys Thr
130 135
```

What is claimed is:

1. A purified nucleic acid molecule derived from the Yaba Monkey Tumor Virus having at least 99% nucleic acid sequence identity to SEQ ID NO:1, wherein said nucleic acid molecule encodes a polypeptide that modulates cytokine function.

2. The nucleic acid molecule of claim 1, wherein said nucleic acid molecule comprises the nucleic acid sequence of SEQ ID NO:1.

3. The nucleic acid molecule of claim 1, wherein said nucleic acid molecule consists of SEQ ID NO:1.

4. A nucleic acid molecule comprising a sequence complementary to a nucleic acid sequence having at least 99% identity to SEQ ID NO:1.

5. The nucleic acid molecule of claim 1, wherein each T is replaced with a U.

6. A vector comprising the nucleic acid molecule of claim 1.

7. The vector of claim 6, wherein said nucleic acid molecule is positioned for expression.

8. The vector of claim 6, wherein said nucleic acid molecule is under the control of an inducible promoter.

9. The vector of claim 6, wherein said vector is suitable for expression in a mammalian cell.

10. A pharmaceutical composition comprising the nucleic acid molecule of claim 1 formulated in a pharmaceutically acceptable carrier in an amount sufficient to treat an immune disorder or inflammation when administered to a cell of a subject.

11. The purified nucleic acid molecule of claim 1, wherein said nucleic acid molecule encodes a Yaba Monkey Tumor Virus polypeptide.

12. The purified nucleic acid molecule of claim 11, wherein said nucleic acid molecule encodes a polypeptide comprising an amino acid sequence having at least 99% amino acid sequence identity to SEQ ID NO:2.

13. The purified nucleic acid molecule of claim 12, wherein said nucleic acid molecule encodes a polypeptide comprising the amino acid sequence of SEQ ID NO:2.

14. The purified nucleic acid molecule of claim 13, wherein said nucleic acid molecule encodes a polypeptide consisting of the amino acid sequence of SEQ ID NO:2.

15. A vector comprising the nucleic acid molecule of claim 11.

16. The vector of claim 15, wherein said nucleic acid molecule is positioned for expression.

17. The vector of claim 15, wherein said nucleic acid molecule is under the control of an inducible promoter.

18. The vector of claim 15, wherein said vector is suitable for expression in a mammalian cell.

19. A vector comprising the nucleic acid molecule of claim 13.

* * * * *

UNITED STATES PATENT AND TRADEMARK OFFICE
CERTIFICATE OF CORRECTION

PATENT NO. : 7,101,559 B2 Page 1 of 1
APPLICATION NO. : 10/455000
DATED : September 5, 2006
INVENTOR(S) : McFadden et al.

It is certified that error appears in the above-identified patent and that said Letters Patent is hereby corrected as shown below:

Column 3, Line 65, replace "features a A method" with --features a method--.

Column 5, Line 1, replace "the the nucleic acid" with --the nucleic acid--.

Signed and Sealed this

Thirteenth Day of February, 2007

JON W. DUDAS
*Director of the United States Patent and Trademark Office*